United States Patent
Hering et al.

(10) Patent No.: US 10,088,062 B2
(45) Date of Patent: Oct. 2, 2018

(54) VALVE, PUMP SYSTEM AND METHOD FOR OPERATION OF A PUMP SYSTEM

(75) Inventors: Joerg Hering, Fredersdorf (DE); Norbert Schwiertz, Strausberg (DE)

(73) Assignee: BERLIN HEART GMBH, Berlin (DE)

( * ) Notice: Subject to any disclaimer, the term of this patent is extended or adjusted under 35 U.S.C. 154(b) by 353 days.

(21) Appl. No.: 13/877,234

(22) PCT Filed: Sep. 30, 2011

(86) PCT No.: PCT/EP2011/005078
§ 371 (c)(1),
(2), (4) Date: Aug. 6, 2013

(87) PCT Pub. No.: WO2012/041525
PCT Pub. Date: Apr. 5, 2012

(65) Prior Publication Data
US 2013/0343917 A1    Dec. 26, 2013

Related U.S. Application Data

(60) Provisional application No. 61/388,842, filed on Oct. 1, 2010.

(30) Foreign Application Priority Data

Oct. 1, 2010    (EP) .................................. 10075607

(51) Int. Cl.
*F16K 11/085*    (2006.01)
*F04B 49/22*    (2006.01)
(Continued)

(52) U.S. Cl.
CPC ......... *F16K 11/0856* (2013.01); *A61M 1/106* (2013.01); *F04B 49/22* (2013.01);
(Continued)

(58) Field of Classification Search
CPC .. F16K 11/076; F16K 11/085; F16K 11/0856; F04B 43/073; F04B 43/0736;
(Continued)

(56) References Cited

U.S. PATENT DOCUMENTS 2,439,515 A * 4/1948 Hodgson ................. B63H 21/22
                                                                137/625.24
2,703,055 A * 3/1955 Veth et al. ..................... 417/205
(Continued)

FOREIGN PATENT DOCUMENTS

| WO | WO89/01600 | * | 2/1989 | ............... F28G 1/12 |
| WO | WO 89/01600 |   | 2/1989 | |
| WO | WO2009150013 | * | 12/2009 | |

*Primary Examiner* — Bryan Lettman
(74) *Attorney, Agent, or Firm* — Brinks Gilson & Lione

(57) ABSTRACT

A valve for the control of a fluid flow may be provided, the valve including a connection block having a cylinder-symmetrical recess, where at least one first and a second entry channel as well as a first and a second exit channel run out in the peripheral surface of the recess. A control pin, which is fitted into the recess, is rotatable about a rotation axis, having at least two through-channels and connecting different ones of the entry and exit channels of the connection block to one another depending on its angular position. A first through-channel in the pin, with respect to the rotation axis, may exclusively connect channels running out at a first axial height, to one another, and a second through-channel exclusively connecting channels running out at a second axial height, to one another.

12 Claims, 5 Drawing Sheets

(51) Int. Cl.
*A61M 1/10* (2006.01)
*A61M 1/12* (2006.01)

(52) U.S. Cl.
CPC .......... *F16K 11/085* (2013.01); *A61M 1/1037* (2013.01); *A61M 1/1087* (2014.02); *A61M 1/12* (2013.01); *A61M 1/122* (2014.02)

(58) Field of Classification Search
CPC .......... F04B 9/08; F04B 45/073; F04B 49/22; F04B 45/0736; A61M 1/106
See application file for complete search history.

(56) References Cited

U.S. PATENT DOCUMENTS

| | | | |
|---|---|---|---|
| 5,232,434 A | | 8/1993 | Inagaki et al. |
| 5,611,462 A | * | 3/1997 | Barkes ................ F16K 11/0856 137/607 |
| 5,931,163 A | * | 8/1999 | Stegmann et al. ....... 128/204.26 |
| 7,690,397 B2 | * | 4/2010 | Hollis ...................... 137/625.47 |
| 8,752,583 B2 | * | 6/2014 | Wagner .................. F02C 7/232 137/625.23 |
| 2006/0118183 A1 | * | 6/2006 | Coley ................ F15B 13/0406 137/625.21 |

* cited by examiner

VALVE, PUMP SYSTEM AND METHOD FOR OPERATION OF A PUMP SYSTEM

CROSS-REFERENCE TO RELATED APPLICATIONS

This application is a 371 nationalization of PCT/EP2011/005078, which in turn claims benefit of U.S. Provisional Application 61/388,842 filed Oct. 1, 2010, and European application 10075607.1 filed Oct. 1, 2010.

BACKGROUND

The invention lies in the field of engineering and relates in particular to fluid valves and hydraulic or pneumatic pump systems which are controlled by way of such valves.

Valves are known in a variety of embodiments for opening and for closing fluid conduits or for the control of hydraulic and/or pneumatic circuits. Such valves differ on account of their loading ability, by the speed of the response or of the actuation possibility, the sealedness, the pressure loadability, and by the number of switching operations which may be carried out without significant wear. The design of such valves with regard to the material selection, the fashion as well as the allowable manufacturing tolerances depends on the individual demands.

With fluid circuits in the pressure range of a few atmospheres excess pressure, sliding valves for example are actuated, with which a slide is translatorily movable in a bore of a connection block and, by way of recesses which are provided in the slide, connects different openings or channels of the connection block to one another depending on the slide position. One may selectively subject different fluid conduits to pressure by way of such a valve.

The play tolerance with the dimensions of such a slide in relation to the bore, in which it moves may be of a magnitude for example of hundredths of millimeters, in order to avoid unallowable leaks. An air cushion effect may form with the movement of such a slide, given a correct dimensioning of the tolerances, and this effect avoids direct contact and wear.

Moreover, a rotary slide valve arrangement for the pneumatic control is known from the German patent document DE 10 2006 011 580 B3 of the company Numatics GmbH, which serves for the control of compressed air and envisages a control slide (control valve) which is rotatable in a cylinder bore and which may be rotated and driven, wherein the control slide comprises surface grooves or inner channels which connect transverse bores in the connection block to one another or separate them from one another, depending on the rotation position. Thereby, a cylinder gap between the cylinder bore in the connection block and the control slide is dimensioned such that a low-friction mounting is given according to the principle of an air bearing.

It is clear from the cited patent document, that in each case different channels in the connection block, which are arranged at different axial heights in relation to the rotation axis of the slide, are connected to one another by way of the slide.

The task often arises of switching pneumatic circuits in a manner such that on the one hand the pneumatic resistance of the conduits and valves is minimised in the different switch position and that on the other hand as constant as possible pneumatic flow resistances are maintained at different switch positions.

A system with two membrane heart pumps as well as a switch-over valve is known from U.S. Pat. No. 5,232,434.

A switch-over valve is known from WO 89/01600 A2, with which channels are switched by way of a control pin in a hollow cylinder. For switching between several channels which lie at different axial heights in the hollow cylinder, a switch channels is used, which in the control pin runs from a first axial position to a second axial position. This entails a design of the control pin which is complex and difficult to manufacture.

It is the object of the present invention, to provide a valve which combines quick and efficient switch-over possibilities with an as minimised as possible flow resistance and with a simple design construction of the valve.

SUMMARY

According to the invention, for this purpose, with a valve for the control of a fluid flow, a connection block is provided, which comprises a cylinder-symmetrical recess, wherein at least one first and a second entry channel as well as a first and second exit channel run out in the peripheral surface of the recess. Moreover, a control pin is provided, which fits into the recess, is rotatable about a rotation axis, comprises at least two through-channels and connects different ones of the entry channels and exit channels of the connection block to one another depending on its angular position. For this, a first through-channel is provided in the pin, and this first through-channel connects channels of the connection block to one another, which exclusively run out at a first axial height with respects to the rotation axis, as well as a second through-channel which connects channels of the connection block to one another, which exclusively run out at a second axial height.

In this manner, it is ensured that in the different switch positions of the pin, the through-channels in each case run exclusively at a single axial height with respect to the rotation axis and that with this, various channels to be switched through have no channel sections which run in the longitudinal direction (direction of the rotation axis) of the pin, so that the direction changes of the through-channels are minimised. The flow resistance of the valve in the different positions is minimised by way of this. Moreover, the through-channels which are to be machined into the pin are very simple to realise with regard to design, since they do not need to include sections running in the longitudinal direction of the pin. They may, for this reason, be realised for example as simple transverse bores in the pins.

Dead volumes on switching-over are kept low since the length of the through-channels may also be kept short by way of this.

A further advantage of such valves which may be actuated by way of rotating a pin lies in the fact that the application of the pressure to be controlled unleashes no force action on the movable elements of the valve. A tendency of the valve to misalign due to the acting pressure is thus not given.

One embodiment of the invention envisages at least one first switch-over channel running out at the first axial height in the peripheral surface of the recess and connecting this run-out to a channel running out at the second axial height, being provided in the connection block.

The run-out of an entry channel, the run-out of an exit channel and the run-out of a switch-over channel are thus provided at the first axial height, wherein the three mentioned channels may be connected to one another in different rotational positions of the control pin. In one switch position, thereby the entry channel may be connected to the exit channel, by which means the valve connects through a fluid conduit between the entry channel and the exit channel in a straight-lined manner.

In another switch position of the pin, the respective entry channel may be connected to a switch-over channel and via this to a second exit channel which runs out at a second axial height within the peripheral surface of the connection block.

This means that the first entry channel may be switched through to a second exit channel. As a whole, this configuration permits a switching of an entry channel through to two exit channels. In this context, one may envisage channels running in the axial direction of the control pin and of the hollow cylinder being provided only in the connection block, and the control pin being free of channels which have a component of their running direction in the axial direction or a section running in the axial direction.

One advantageous design of the invention envisages at least one through-channel, in particular the first and the second through-channel, running transversely through the pin between a first and a second pin opening lying diametrically opposite one another, and comprising a branch-off channel which ends at a third pin opening.

A part of the through-channel may thus be incorporated into the pin in a simple manner by way of incorporating a transverse bore. A branch-off channel which forms a further part of the through-channel, may furthermore be incorporated in a simple manner by way of incorporating a radial bore into the pin, said radial bore being incorporated so deeply from the peripheral surface of the pin perpendicularly to the longitudinal axis, that it hits the channel which for example runs centrally and transversely through the pin.

With this, a T-shaped or Y-shaped channel leading of the through-channel results, wherein all limbs of the through-channel run at the same axial height on a cross-sectional plane of the pin and run out in three openings on the peripheral surface of the pin, of which for example two lie diametrically opposite one another on the periphery of the pin and a third laterally symmetrically or asymmetrically between the first-mentioned two openings.

In this context, the distribution of the openings of the through-channels is directed to the arrangement of the respective run-outs of entry and exits channels or of further channels in the inner peripheral surface of the recess in the connection block.

Moreover, one may advantageously envisage at least one second switch-over channel being provided in the connection block, said second switch-over channel running out at the second axial height in the peripheral surface of the recess and connecting this run-out to a channel running out at the first axial height. With this, it is possible by way of the pin, at the second axial height, for the second entry channel to either be switched through to the second exit channel or for the second entry channel to be connected to a switch-over channel which runs out at the second axial height and which for its part is connected to a channel running out at the first axial height. This channel running out at the first axial height may for example be the first exit channel, so that the second entry channel may be connected to the first exit channel in a suitable switch position.

In a particularly advantageous design of the invention, one may envisage the pin having a third through-channel.

With this design, one may also envisage the third through-channel connecting two sections of a switch-over channel to one another depending on the angular position of the pin.

With this, it is possible not only to utilise the switch-over channels by way of suitable positions of the pin and thus to create a cross-over assignment of the entry channels to the exit channels, but additionally to simultaneously switch at least one of the switch-over channels by way of this switch-over channel running through the pin in sections. With this, it is possible in the switch positions, in which the entry channels are each switched through in a straight-lined manner, to close at least one of the switch-over channels and thus to prevent a flowing-over between the channels to be switched.

The third switch-over channel is advantageously provided at an axial height between the first and the second axial height within the pin, as a transverse bore.

The invention may furthermore be advantageously developed by way of the connection block comprising a valve hollow cylinder which receives the pin and seals for sealing the channels between the pin and the connection block.

The connection block is accordingly provided with a valve hollow cylinder which forms an insert and for its part on its inner peripheral surface forms the recess for the control pin. The valve hollow cylinder may comprise sealing elements, such as for example elastomer seals, on its inner peripheral surface, which at the different angular positions of the pin, seal the respective channel run-outs to be connected.

For example, the valve hollow cylinder may also comprise peripheral elastomer seals in the peripheral direction of the pin, which basically close off the groups of channel run-outs at different axial heights with respect to the rotation axis of the pin. Instead of elastomer seals, one may also provide other seals which with regard to dimensional tolerance are designed in a manner such that an efficient sealing is given with low friction formation. The valve in the ideal case should be in the position of switching, with reaction times in the millisecond region, different pneumatic channels by way of changing the angular position of the pin.

The separate valve hollow cylinder has the advantage that it may be well separately machined and be provided with inserts of other materials, before it is inserted into the connection block. The valve hollow cylinder in operation is immovably connected to the remaining parts of the connection block. It has only radially continuous openings which respectively form a part of the entry channels, exit channels and switch-over channels.

The remaining part of the connection block comprises the continuations of the entry channels and exit channels as well as switch-over channels, which at least partly also run in the longitudinal direction of the control pin, in order to create the connections between the channels running out at the first height and at the second height.

This part of the connection block may be designed as a solid block through which milled channels pass and may for example consist of metal. The manufacture from a stable plastic or a ceramic is also possible.

In order to render the control pin driveable in a rotary manner, according to the invention, one advantageously envisages the control pin at its ends being connected to a magnet which forms part of a rotation drive. In this context, the control pin may end in a shape body, onto which a permanent magnet is applied, which, with a switchable electromagnet, assumes its different switch positions depending on the magnetic field of the electromagnet.

Moreover, it may be advantageous to provide mechanical abutments between the pin and the connection block which define two end angle positions of the pin.

The rotational positions/angular positions of the control pin may be defined in a sufficiently accurate manner by way of mechanical abutments, in order to bring the run-outs of the channels in the peripheral surfaces of the pin and recess into congruence and with this to keep the pneumatic resistance low. With this, the demands on the accuracy of the drive are reduced with the setting of the different angular positions.

One may also set preferred intermediate positions between the end positions of the pin which are defined by the abutments, by way of these positions being characterised and stabilised by a ball lock between the pin and the connection block.

The invention, apart from relating to a valve of the type described above, also relates to a pump system with two pump drives, which are each connectable by way of fluid conduits to one working pump for conveying a fluid, in particular blood, wherein both fluid conduits run through a common valve of the type described above and the valve is designed as a 2×2-way cross-over valve.

In this context, the drive pumps may be designed as membrane pumps which assume changing membrane positions due to a changing fluid pressure of a working pump, and develop a pulsating pump effect on account of this. For example, membrane pumps which may be applied in the human body as blood pumps and which may assist the activity of the heart, are based on this principle. The setting of the membrane is effected via the control of a secondary pressure by way of a working pump which is designed as a pneumatic pump and is connected to the respective drive pump by way of a fluid conduit. Two drive pumps are required in biventricular operation of such pumps, which are applied to different heart chambers and are each connected to one working pump.

If one of the working pumps fails, then the remaining intact working pump may be switched through to the two drive pumps in an alternating manner by way of a 2×2-way cross-over valve, so that both heart chambers may continue to be assisted.

Inasmuch as this is concerned, the invention also relates to a method for the operation of a pump system with a valve of the described type which is connected to at least one operational drive pump and to two working pumps and is designed as a 2×2-way cross-over valve, characterised in that the valve alternatingly connects a drive pump to each of one of the working pumps.

BRIEF DESCRIPTION OF THE DRAWINGS

The invention is hereinafter shown by way of an embodiment example in the drawings and described hereinafter.

Thereby are shown in.

DESCRIPTION OF A PREFERRED EMBODIMENT

Figure 1:
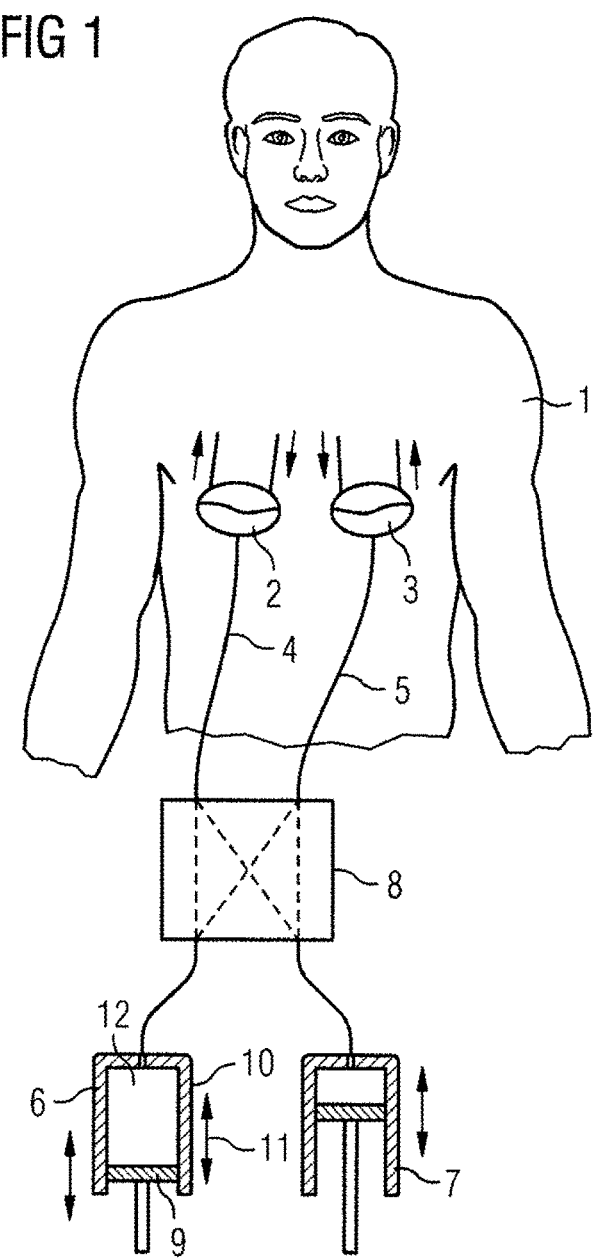
FIG. 1 schematically, a pump system with two drive pumps and two working pumps which are applied as blood pumps with a human patient, FIG. 2 a more detailed representation of a membrane working pump, FIG. 3 a schematic representation of the channels in a valve, FIG. 4 a schematic representation of crossed channels in a valve, FIG. 5 a schematic representation of a valve with a continuous and with a blocked channel, FIG. 6 a schematic representation of a valve with a switched-over channel, FIG. 7 a schematic representation of a valve with a second continuous channel, wherein the first channel is blocked, FIG. 8 a schematic representation of a valve, wherein the second channel is switched over, FIG. 9 a three-dimensional view of a connection block, FIG. 10 three three-dimensional views of the same valve cylinder from different viewing angles, FIG. 11 three three-dimensional views of a control pin from different viewing angles, FIG. 12 schematically, below one another, three cross sections of a valve with a control pin at three axial heights, in which through-channels are arranged in the control pin, inlet channels and outlet channels, FIG. 13 the representation of FIG. 12 with equally lying cross sections, wherein the control pin is rotated by 90° in the clockwise direction with respect to the representation in FIG. 12, FIG. 14 a partly broken view of the connection block with the control pins which are visible therein, FIG. 15 a schematic view of the control pin with symbolically represented switch-over channels as well as FIG. 16 the arrangement of FIG. 15, represented from the opposite viewing direction.

FIG. 1 symbolically shows the silhouette 1 of a human with two membrane pumps 2, 3, of which in each case one is connected to a blood vessel, as well as two corresponding pneumatic supply conduits 4, 5, via which the membrane pumps 2, 3 are connected in each case to a drive pump 6, 7. Moreover, a valve 8 is represented schematically, which is designed as a 2×2-way cross-over valve.

In a first switch position, the valve 8 connects the drive pump 6 to the working pump 2, and the drive pump 7 to the working pump 3.

In a second switch condition, the valve 8 connects the drive pump 6 to the working pump 3, and the drive pump 7 to the working pump 2.

By way of this switching possibility, the complete system may be operated with only one drive pump 6, 7 in the case that one of the drive pumps 6, 7 fails, with biventricular operation when the function of a heart chamber is assisted by each one of the working pumps 2, 3. In this case, the remaining intact drive pump 6, 7 is switched-over in an alternating manner to the working pumps 2, 3 by way of the valve 8, so that each of the working pumps may assist two heart beats or works through two pulsatile periods.

The drive pumps 6, 7 are designed as pneumatic piston pumps each with a piston 9 and with a cylinder 10, wherein the piston 9 may be driven in an alternating manner in the direction of the arrow 11 by way of a drive which is not shown in more detail, in order in the drive volume to alternatingly produce a vacuum and excess pressure which is led in each case to one of the membrane pumps 2, 3 by way of the pneumatic conduit 4, 5.

Figure 2:
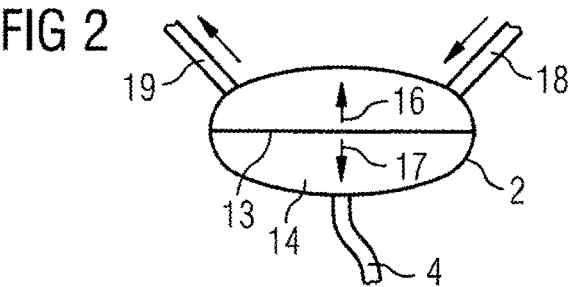

The construction of a membrane pump 2 is described in more detail in FIG. 2. This has a flexible membrane 13 which separates a drive space 14 from a working space 15. The membrane 13 is flexible and is coated with a substance which prevents the coagulation of blood.

The drive space 14 is connected directly to a supply conduit 4 which by way of the supply and discharge of a gas, in particular air, ensures that the drive space 14 enlarges and reduces in an alternating manner and, with this, this the membrane moves in the direction of the arrows 16, 17.

The working space 15 is forced to reduce in size when the drive space 14 increases in size and vice versa. Blood is sucked into the working space 15 by way of the blood supply conduit 18 by way of this, and this blood is ejected again through the blood discharge conduit 19 with a reduction of the working volume 19. One-way check valves in the supply conduit 18 and the discharge conduit 19 ensure that the blood flow is directed in an unambiguous manner.

Figure 3:
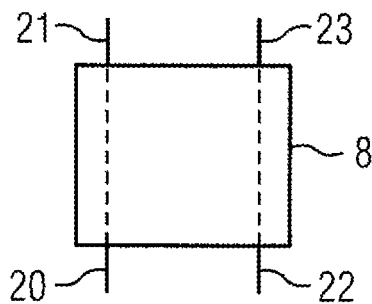

FIG. 3 shows a schematic representation of the valve 8, in which a first inlet channel 20 is connected to a first outlet channel 21, and a second inlet channel 22 is connected to a second outlet channel 23. The inlet channel 20 may be connected to the working pump 6, and the outlet channel 21 to the working pump 2, whilst the inlet channel 22 is connected to the drive pump 7, and the outlet channel 23 to the drive pump 3.

Figure 4:
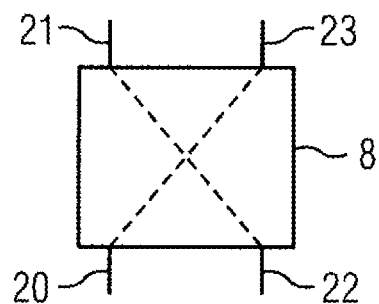

FIG. 4 shows another switch condition of the valve 8, in which the first inlet channel 20 is connected to the second outlet channel 23, and the second inlet channel 22 to the first outlet channel 21, as is symbolised by the switch-over channels represented in a dashed manner.

Figure 5:
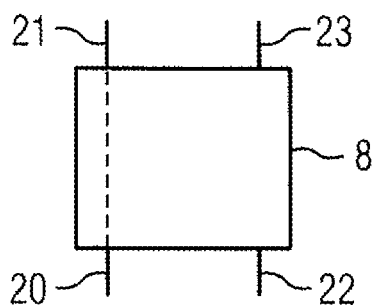

FIG. 5 shows a representation, in which the first inlet channel 20 is connected to the first outlet channel 21, wherein the fluid delivery from the second inlet channel 22 to the second outlet channel 23 is not represented, since the drive pump 7 is assumed to be incapable of functioning. With this, gas exclusively flows from the first inlet channel 20 to the first outlet channel 21 and back, and only the working pump 2 is operated.

Figure 6:
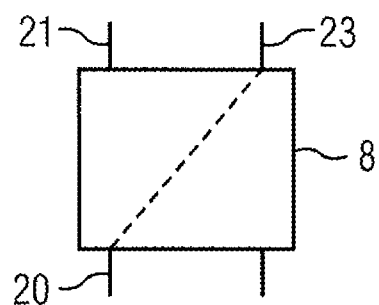

FIG. 6 shows the switched-over condition of the valve 8, in which the first inlet channel 20 is connected to the second outlet channel 23 and, so is connected via the supply conduit 5 to the second working pump 3, so that the second working pump 3 may be supplied by way of the drive pump 6.

Figure 7:
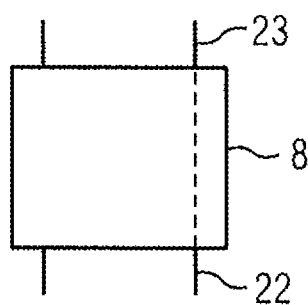

FIG. 7 shows an alternative case, in which the drive pump 7 is intact and may be connected via the valve 8 by way of the inlet channel 22 via the outlet channel 23 to the working pump 3.

Figure 8:
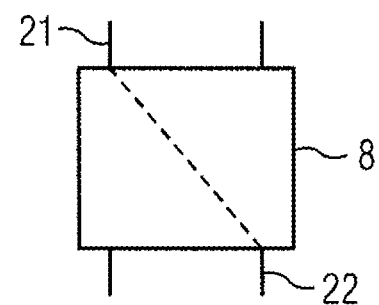

After switching over the valve 8, as is represented in FIG. 8, this condition leads to the second inlet channel 22, as is shown in a dashed manner, being connectable to the first outlet channel 21, so that the working pump 2 may be driven by way of the drive pump 7.

Figure 9:
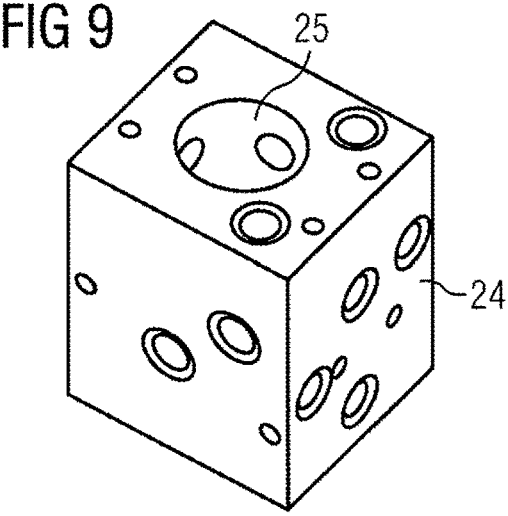
Figure 10:
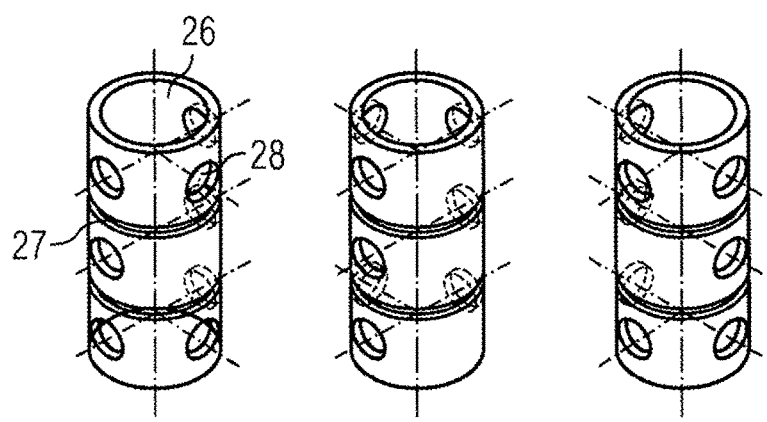

FIG. 9 shows the connection block 24 which comprises a cylindrical bore 25 into which a valve cylinder 26 which is shown in FIG. 10 may be inserted in a sealed manner. Moreover openings, in which inlet and outlet channels or switch-over channels run out, are represented in the connection block 24.

The respective channels may run within the connection block 24 in a straight or bent or angularly bent manner, and specifically within a plane at a constant axial height with respect to the rotation axis of the control pin or also in the axial direction.

FIG. 10, in three views from different viewing angles, shows the valve cylinder 26 which is designed as a hollow cylinder and comprises grooves 27 for receiving sealing rings which serve for sealing the valve cylinder in the connection block 24. Moreover, the valve cylinder 26 comprises openings 28 which pass through the hollow cylinder and connect the outer peripheral surface to the inner peripheral surface in the radial direction. In this context, openings are provided at three different axial heights, with respect to the longitudinal axis of the valve cylinder. Therein, two openings are provided at the middle axial height, which lie diametrically opposite one another. Three openings which are offset to one another by 90° on the periphery are each provided at the first and the second axial height, i.e. at the two ends of the valve cylinder.

Figure 11:
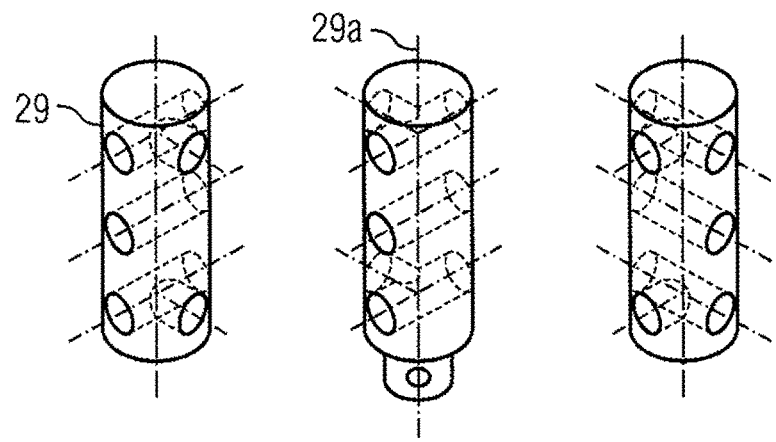

A control pin 29 is represented in FIG. 11 in three three-dimensional representations from different viewing angles, wherein the through-direction of three through-channels is visible in the middle representation, wherein these through-channels each completely pass through the control pin in a transverse manner. Moreover, additionally, transversely running bores which run out in the previously mentioned channels, are arranged at the first and second axial height. Three openings/run-outs of the through-channels which are offset for example by 90° on the periphery of the control pin, result each at the first and second axial height.

Radially peripheral grooves are represented between the three different planes, in which the through-channels are arranged, and these grooves serve for receiving sealing rings which after the insertion of the control pin into the valve cylinder 26 serve for sealing.

Three cross sections through the control pin 29 and the valve cylinder 26 surrounding this are represented below one another in FIG. 12, from the top to the bottom at the first, third (middle) and second axial height, wherein these two elements are imagined in the connection block 24. The valve cylinder 26 is represented symbolically merely as a circular line, with the respective radial openings which are in each case represented only as short lines 30, 31, 32.

Respective channels are indicated in the second section at 33, 34 and in the third section at 35, 36, 37.

The through-channels at the different axial heights of the control pin are indicated at 38, 39, 40 (continuous transverse bores) as well as 41, 42 (branch-off channels). FIG. 12 shows an angular position of the control pin 29, in which a first inlet channel 20 is directly connected to a first outlet channel 32 by way of the through-channel 38 in the control pin. The branch-off channel 41 ends blindly and plays no part in this angular position.

In this angular position of the control pin 29, a lever 43 connected to the control pin 29 leans on an abutment 44 formed as a pin, in order to define the angular position.

Figure 12:
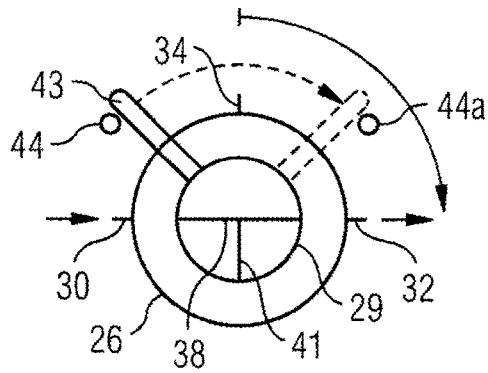
Figure 12:
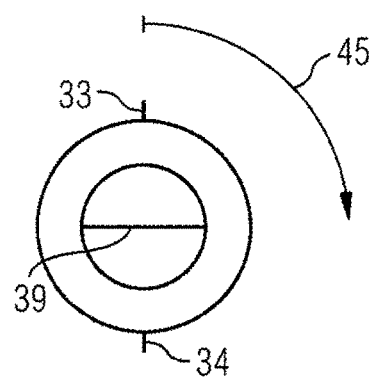
Figure 12:
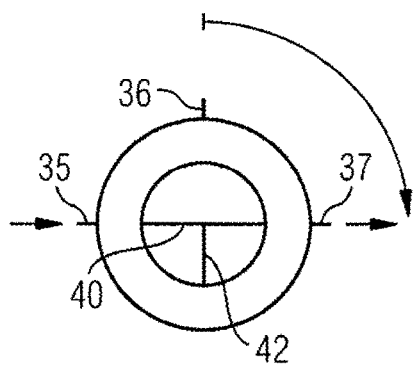

Simultaneously, a switch-over channel which ends in the openings 33, 34 of the middle section of FIG. 12, is interrupted, since no corresponding through-channels exist in the pin 29 which are suitably positioned in this switch position.

In the third section of FIG. 12, it is shown that the second inlet channel 35 is connected directly to the second outlet channel 37 by way of the through-channel 40, at the second axial height of the second inlet channel 35. The branch-off channel 42 ends in a likewise blind manner in this switch position.

The openings 31, 36 in the valve cylinder, and the corresponding channels leading further in the connection block likewise have no function in this switch position.

This switch position may also be considered as a basic switch position, in which the entry channels are connected directly to the respective exit channels with the shortest path and low as possible flow resistance, so that the drive pumps 6, 7 are connected through in each case to their working pumps 2, 3.

The valve 8 is switched by way of the control pin 29 being rotated in the clockwise direction and in the direction of the arrow 45 by 90°, as is indicated in FIG. 12. Thereby, other angular positions are also possible, wherein the angles between the through-channels, branching channels and the entry and exit channels must then be adapted accordingly.

Figure 13:
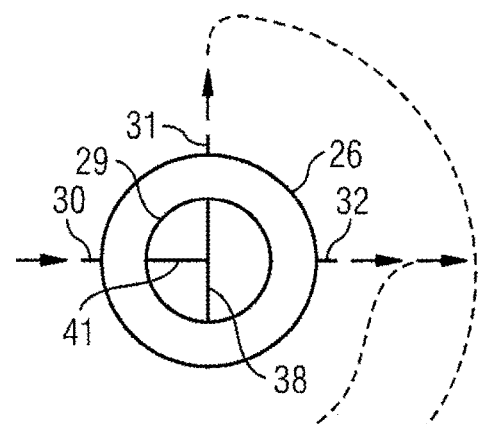
Figure 13:
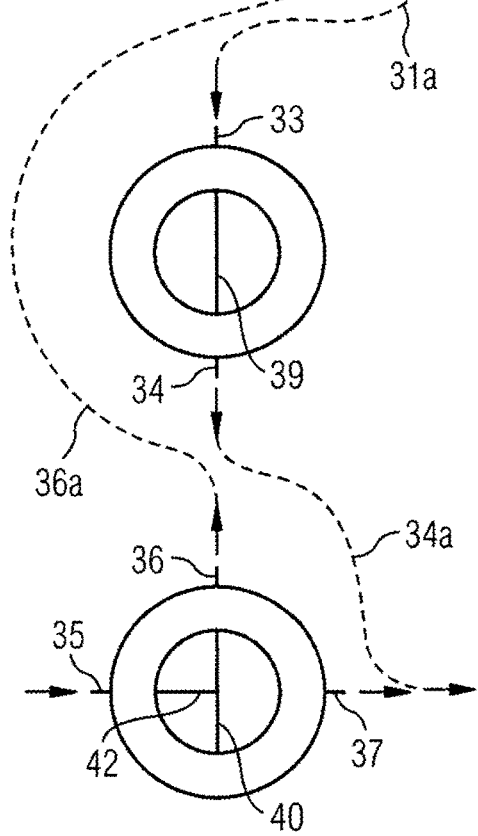

The switch position rotated by 90° is represented in FIG. 13. The upper cross section is FIG. 13 is firstly considered. The through-channel 38 now no longer connects the first inlet channel 30 to the first outlet channel 32. Rather, the inlet channel 30 is connected to the opening 31 in the valve cylinder, into which a switch-over channel 31 runs out. The switch-over channel 31a runs in the connection block 24 at least partly also in the axial direction of the control pin and connects the opening 31 at the first axial height, to the opening 33 at the middle axial height, as is represented in the middle cross section in FIG. 13. The opening 33 in the valve cylinder in the switch position represented in FIG. 13 is aligned flush with the through-channel 39 of the control pin, so that the switch-over channel 39 is connected to the switch-over channel 34a which departs from the opening 34 and leads to the second outlet channel 37. In this manner, the first inlet channel 30 is connected to the second outlet channel 37. Simultaneously, as is visible in the lower cross section of FIG. 13, the second outlet channel 37 is no longer connected via the control pin to the second inlet channel 35. In this position of the control pin, rather the second inlet channel 35 is connected by way of the branch-off channel 42 and a part of the through-channel 40 to the opening 36 and the switch-over channel 36. The switch-over channel 36a for its part is connected to the first outlet channel 32.

Thus in the switch position represented by way of FIG. 13, the 2×2-way cross-over valve is completely switched-over, so that the entry channels are alternatingly switched over to the outlet channels.

If now one of the drive pumps 6, 7 which are connected to the inlet channels 30, 35 fails, then the remaining drive pump may be alternatingly switched over to the two outlet channels 32, 37 and thus to the working pumps which are connected to these, by way of switching over between the positions represented in FIG. 12 and FIG. 13.

Figure 14:
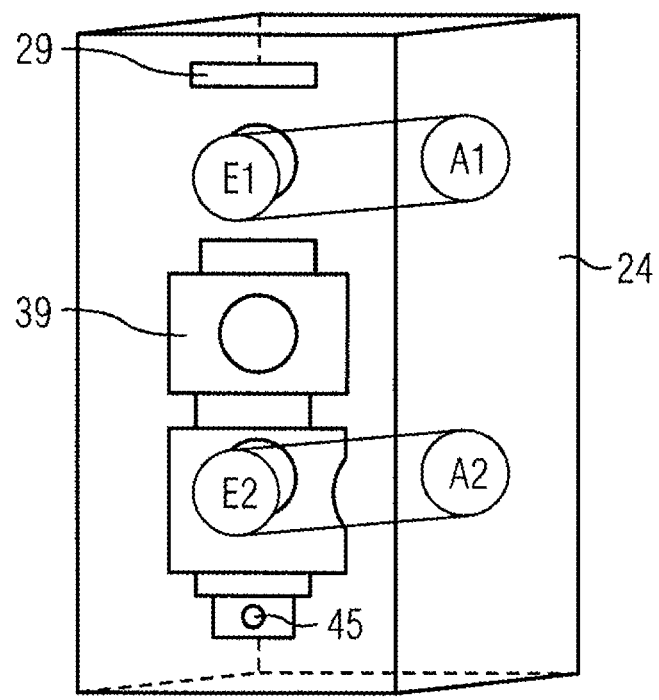

To round off, the connection block 24 is shown in a sectioned representation in FIG. 14, wherein the control pin 29 is shown whilst leaving out the valve cylinder. The first entry channel is indicated at E1, the first exit channel at A1, the second entry channel at E2 and the second exit channel at A2. The through-channel 39 is also shown.

A shape body 45 is shown at the lower end of the control pin 29 and on which a permanent magnet which is not shown is fastened, wherein this permanent magnet may be driven in rotation by way of an electromagnet, in order to move the control pin between the switch positions.

Figure 15:
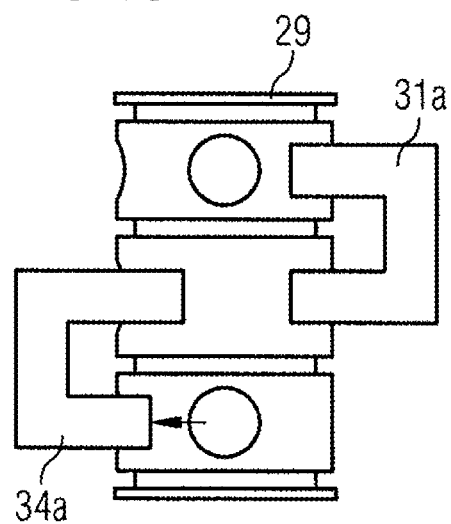
Figure 16:
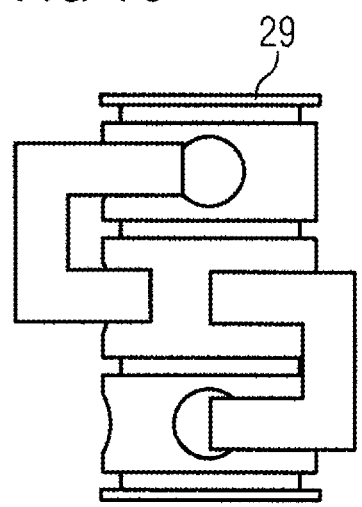

FIG. 15 in a schematic view shows the control pin 29 with switch-over channels 31a, 34a which run in the connection block, and FIG. 16 shows the respective representation in the opposite viewing direction.

A reliably switchable valve for use with pneumatically activated blood pumps and which also has the required service life may be created by way of the represented embodiment of a 2×2-way cross-over valve. Friction and wear may for example be optimised by way of the surfaces being based on ceramic with aluminium or elematate coating, with a suitable dimensional tolerance.

The invention claimed is:

1. A valve to control a fluid flow, the valve comprising:
a connection block comprising a cylinder-symmetrical recess, wherein at least a first and a second entry channel as well as at least a first and a second exit channel run out in a peripheral surface of the recess; and
a control pin, which is fitted into the recess, is rotatable about a rotation axis, comprises at least two through-channels and connects different ones of the entry and exit channels of the connection block to one another depending on an angular position of the control pin about the rotation axis, wherein a first through-channel of the at least two through-channels in the control pin exclusively connects channels of the connection block running out at a first axial height with respect to the rotation axis to one another, and a second through-channel of the at least two through-channels in the control pin exclusively connects channels of the connection block running out at a second axial height with respect to the rotation axis to one another,
wherein the connection block further comprises at least one first switch-over channel running out at the first axial height in the peripheral surface of the recess, the at least one first switch-over channel exclusively connects to one of the entry or exit channels of the connection block running out at the second axial height, and the first switchover channel exclusively extends within the connection block between the peripheral surface of the recess and an outer peripheral surface of the connection block from the first axial height to the one of the entry or exit channels of the connection block running out at the second axial height into the control pin or into one of the at least two through-channels of the control pin.

2. The valve according to claim 1, wherein the first and the second through-channels run transversely through the pin between, in each case, a first and a second pin opening lying diametrically opposite one another, and each of the first and second through-channels comprises a branch-off channel which ends at a third pin opening.

3. The valve according to claim 1, wherein in the connection block, at least one second switch-over channel running out at the second axial height in the peripheral surface of the recess is provided, which connects to one of the entry or exit channels running out at the first axial height.

4. The valve according to claim 1, wherein the pin comprises a third through-channel.

5. The valve according to claim 4, wherein the at least one switch-over channel comprises a switch-over channel, the third through-channel connects two sections of the switch-over channel to one another, depending on the angular position of the pin.

6. The valve according to claim 4 wherein the third through-channel runs at an axial height between the first and the second axial height.

7. The valve according to claim 1 wherein the connection block comprises a valve hollow cylinder which forms the cylinder-symmetrical recess, receives the pin and comprises seals for sealing the channels between the pin and the connection block.

8. The valve according to claim 1 wherein the control pin is connected at one of its ends to a magnet which forms a part of a rotary drive.

9. The valve according to claim 1 wherein mechanical abutments are provided between the pin and the connection block, which define two end angle positions of the pin.

10. A pump system with two drive pumps which are connectable by way of fluid conduits in each case to a working pump for delivering a fluid, wherein both fluid conduits run through a common valve according to one of the claims 1 to 9, and the valve is designed as a 2×2-way cross-over valve.

11. A valve to control a fluid flow, the valve comprising:
a connection block comprising a cylinder-symmetrical recess, wherein at least a first and a second entry channel as well as at least a first and a second exit channel run out in a peripheral surface of the recess; and
a control pin fitted into the recess is rotatable about a rotation axis and comprises at least two through-channels and connects different ones of the entry and exit channels of the connection block to one another depending on an angular position of the control pin about the rotation axis, wherein a first through-channel of the at least two through-channels in the control pin exclusively connects channels of the connection block running out at a first axial height with respect to the rotation axis to one another, and a second through-channel of the at least two through-channels in the control pin exclusively connects channels of the connection block running out at a second axial height with respect to the rotation axis to one another, wherein the connection block further comprises at least one first switch-over channel running out at the first axial height in the peripheral surface of the recess, the at least one first switch-over channel exclusively connects to one of the entry or exit channels of the connection block running out at the second axial height into the control pin or into one of the at least two through-channels of the control pin, the at least one first switch-over channel exclusively extending between the peripheral surface of the recess and an outer peripheral surface of the connection block from the first axial height to the second axial height, and wherein the first and the second through-channels run transversely through the pin between, in each case, a first and a second pin opening lying diametrically opposite one another, and each of the first and the second through-channels comprises a branch-off channel which ends at a third pin opening.

12. A valve to control a fluid flow, the valve comprising:
a connection block comprising a cylinder-symmetrical recess, wherein at least a first and a second entry channel as well as at least a first and a second exit channel run out in a peripheral surface of the recess; and a control pin fitted into the recess is rotatable about a rotation axis and comprises at least two through-channels and connects different ones of the entry and exit channels of the connection block to one another depending on an angular position of the control pin about the rotation axis, wherein a first through-channel of the at least two through-channels in the control pin exclusively connects channels of the connection block running out at a first axial height with respect to the rotation axis to one another, and a second through-channel of the at least two through-channels in the control pin exclusively connects channels of the connection block running out at a second axial height to one another, wherein the connection block further comprises a switch-over channel running out at the first axial height in the peripheral surface of the recess, the switch-over channel exclusively connects to one of the entry or exit channels of the connection block running out at the second axial height with respect to the rotation axis and into the control pin or into one of the at least two through-channels of the control pin, the switch-over channel exclusively extending between the peripheral surface of the recess of the connection block and an outer peripheral surface of the connection block from the first axial height to the second axial height, wherein the control pin comprises a third through-channel that connects two sections of the switch-over channel to one another depending on the angular position of the pin.

* * * * *